US00PP34709P2

(12) United States Plant Patent
Merida

(10) Patent No.: US PP34,709 P2
(45) Date of Patent: Nov. 1, 2022

(54) ***SPATHIPHYLLUM WALLISII* PLANT NAMED 'LUCIA'**

(50) Latin Name: *Spathiphyllum wallisii*
Varietal Denomination: Lucia

(71) Applicant: Michael Merida, Miami, FL (US)

(72) Inventor: Michael Merida, Miami, FL (US)

(73) Assignee: Costa Farms, LLC, Miami, FL (US)

( * ) Notice: Subject to any disclaimer, the term of this patent is extended or adjusted under 35 U.S.C. 154(b) by 0 days.

(21) Appl. No.: 17/803,143

(22) Filed: Mar. 4, 2022

(51) Int. Cl.
*A01H 5/12* (2018.01)
*A01H 6/10* (2018.01)

(52) U.S. Cl.
USPC ..... Plt./364

(58) Field of Classification Search
USPC ..... Plt./364
CPC ... A01H 5/12; A01H 5/02; A01H 5/00; A01H 5/10; A01H 6/00; A01H 6/10; A01H 6/12
See application file for complete search history.

(56) References Cited

U.S. PATENT DOCUMENTS

PP9,944 P * 7/1997 Cornelis ..... Plt./364

* cited by examiner

*Primary Examiner* — June Hwu
(74) *Attorney, Agent, or Firm* — Adrienne Love

(57) ABSTRACT

A new and distinct *Spathiphyllum wallisii* cultivar named 'Lucia' is disclosed, characterized by variegated leaves with two monochromatic colors, yellow and green. The new variety is an *Spathiphyllum wallisii*, normally produced as an ornamental plant.

3 Drawing Sheets

Latin name of the genus and species of the plant claimed: *Spathiphyllum wallisii.*

Varietal denomination: 'Lucia'.

BACKGROUND OF THE INVENTION

The present invention relates to a new and distinct cultivar of *Spathiphyllum*, botanically known as *Spathiphyllum wallisii*, and hereinafter referred to by the name 'Lucia.'

The new *Spathiphyllum* plant cultivar was discovered by Michael Merida in December 2019 in a greenhouse in a plant nursery in Miami, Fla. The instant plant was the result of a whole plant mutation that was naturally occurring. Asexual reproduction of the 'Lucia' by vegetative divisions was first performed in December 2019 and has shown that the unique features of this cultivar are stable and reproduced true to type in successive generations of asexual reproduction.

SUMMARY OF THE INVENTION

The cultivar 'Lucia' has not been observed under all possible environmental conditions. The phenotype may vary somewhat with variations in environment such as temperature, day length, and light intensity without, however, any variance in genotype.

The following traits have been repeatedly observed and are determined to be the unique characteristics of 'Lucia.' These characteristics in combination distinguish 'Lucia' as a new and distinct *Spathiphyllum wallisii* cultivar:

1. Variegated leaves, with moderate green leaves with pronounced variegated margins of pale-yellow green color.

2. Patch of moderate to pale yellow green color, of varying shape and size on either side of the midrib, on moderate green background on a single leaf.
3. Large ovate/egg-shaped leaf with a pointy top.

Plants of 'Lucia' can be compared to plants of the *Spathiphyllum* Plant Named 'Domino,' disclosed in U.S. Plant Pat. No. 9,944. In a side-by-side comparison, however the new 'Lucia' differs from the plants of 'Domino' in the following characteristics:

1. Plants of 'Lucia' produced variegated leaves that have two colors, where the primary color is moderate green, and the secondary color is moderate to pale yellow green. Plants of 'Domino' produce green and white variegated leaves.
2. Plants of 'Lucia' display larger egg-shaped leaves with a pointy top, whereas plants of 'Domino' have smaller narrower elliptic shaped leaves with an acuminate tip.

BRIEF DESCRIPTION OF THE PHOTOGRAPHS

The accompanying colored photographs illustrate the overall appearance of the new *Spathiphyllum* showing the colors as true as it is reasonably possible to obtain in color reproductions of this type. Colors in the photograph may differ slightly from the color values cited in the detailed botanical description of the new variety which accurately describes the colors of the new *Spathiphyllum* plant.

DETAILED BOTANICAL DESCRIPTION OF THE NEW VARIETY

Figure 1:
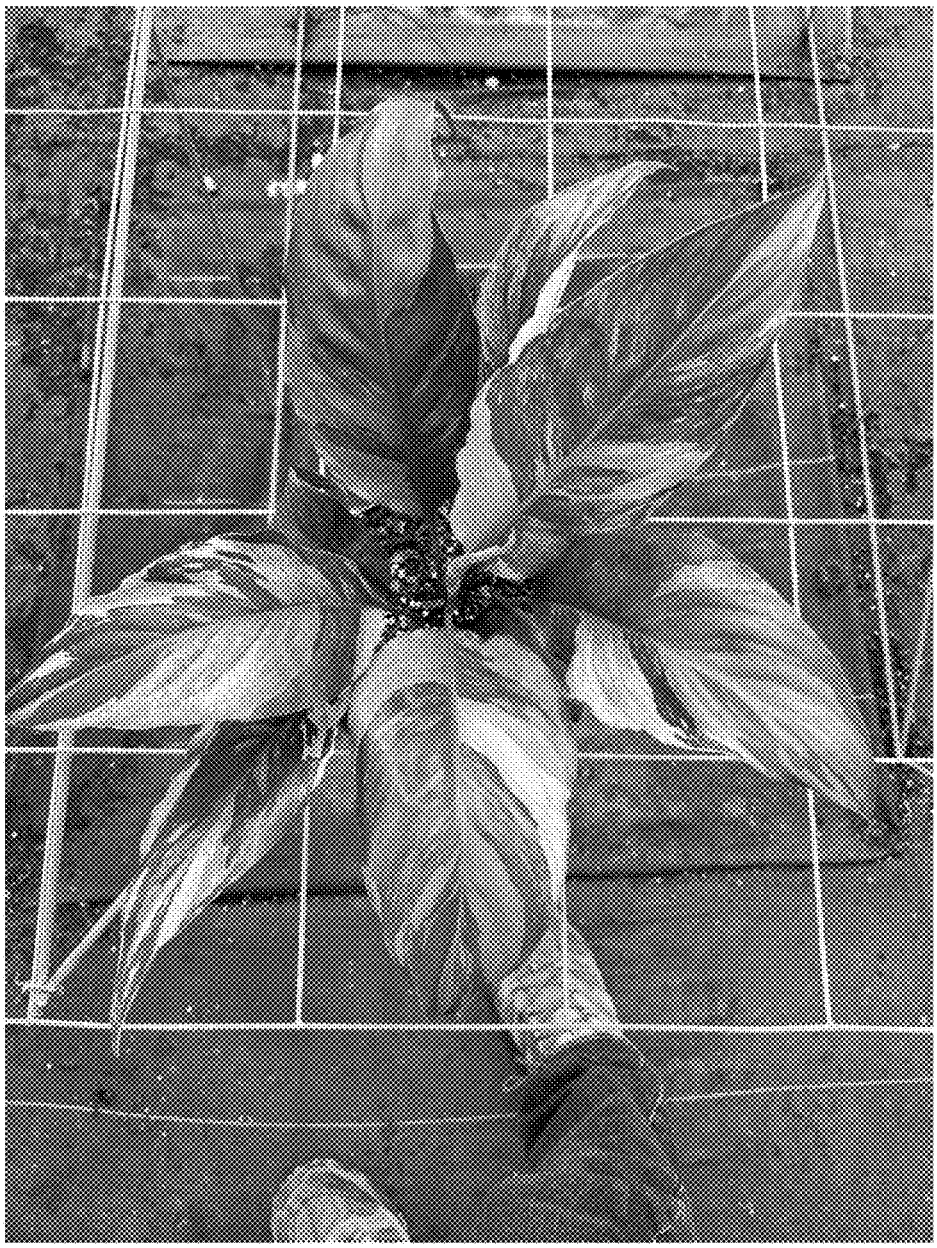
FIG. 1 is a perspective view of a typical plant of 'Lucia', grown in a 15 cm diameter container.
Figure 2:
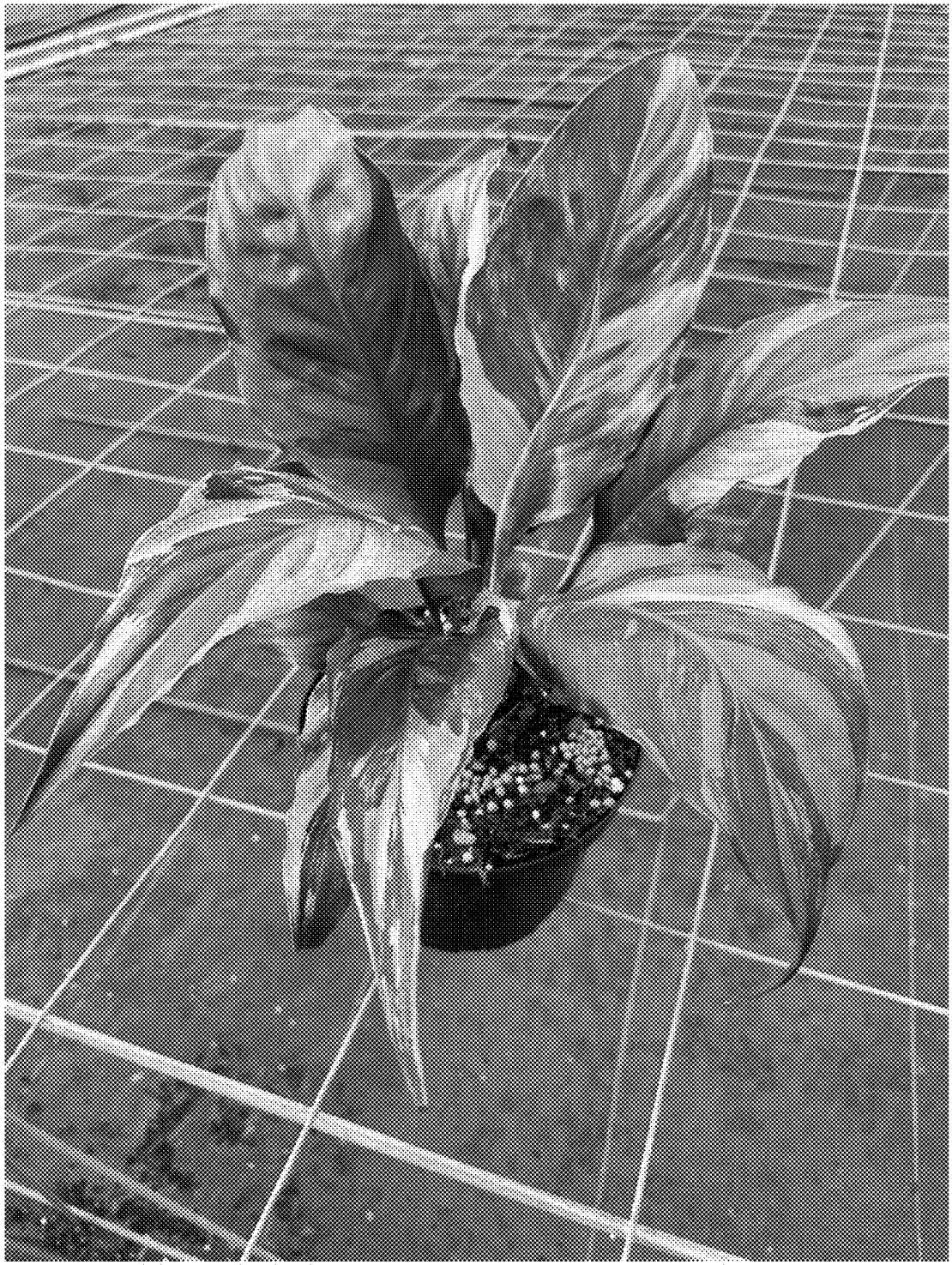
FIG. 2 is a perspective view of a typical foliar variegation of 'Lucia', illustrating the variegation of the leaves.
Figure 3:
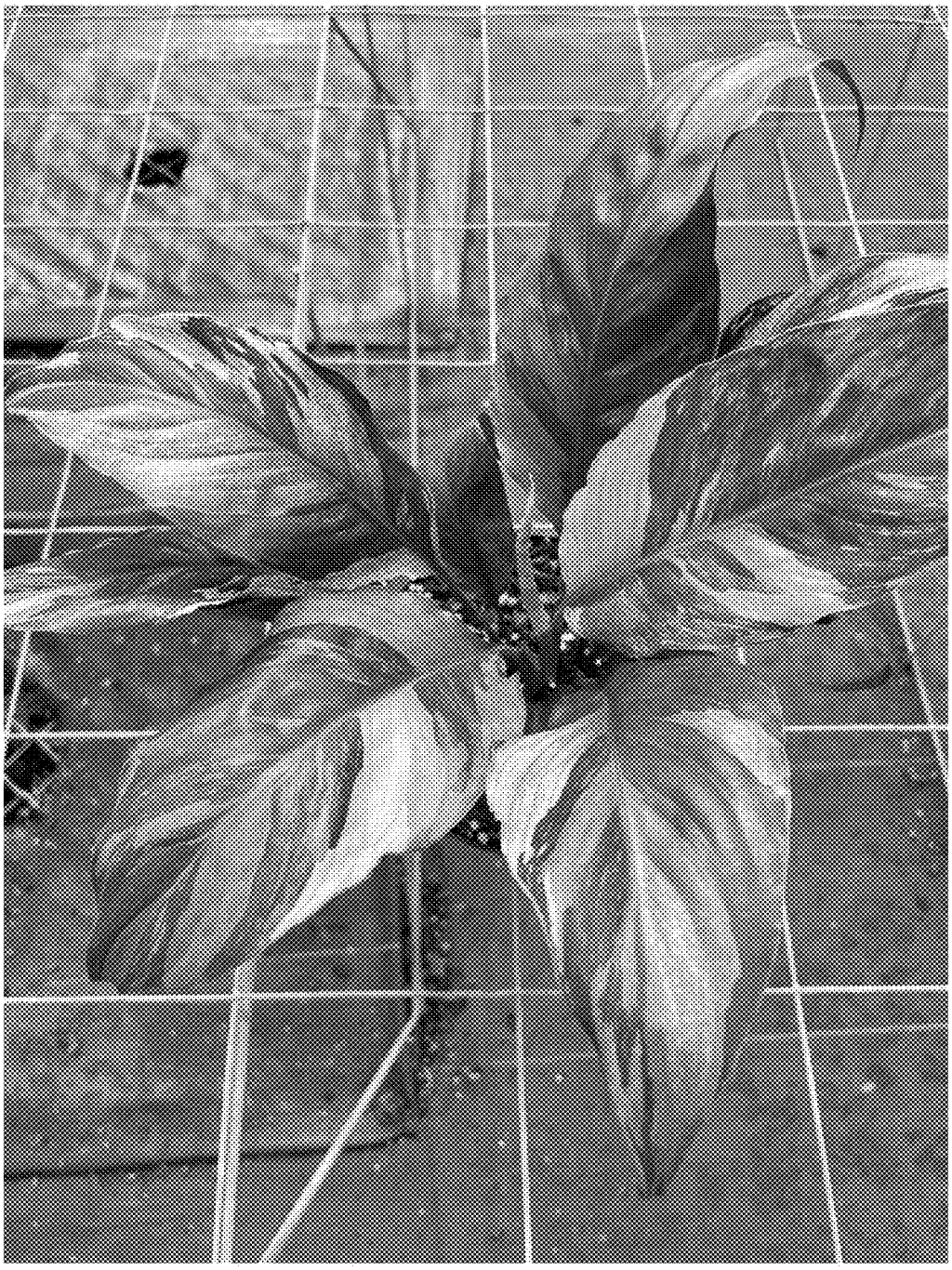
FIG. 3 is a perspective view of a typical foliar variegation of 'Lucia', illustration the variegation, length and width of the leaves.

The aforementioned photographs and the following observations, measurements, and values describes plants of the new *Spathiphyllum* were grown in Miami, Fla. USA in conditions of 80% shading and 24 hr ventilation all year around in 15 cm containers and under cultural practices of commercial *Spathiphyllum* production. During the production of the plants, temperatures ranged from about 20 (winter)-40 (highest in summer) degrees Celsius and light levels were normal sunlight.

Plants were growing about 6 months when the photographs and the description were taken. Even after further growth, the characteristics of the 'Lucia' as described remain true.

The following is a detailed description of the new plant characteristics with color in terminology in accordance with The Royal Horticultural Society Colour Chart, Edition V (2007), except where ordinary dictionary significance of color is indicated.

Botanical classification: *Spathiphyllum walhsii.*

Common name: 'Lucia'.

Botanical Description

Average height of plant: 30-40 cm.
Habit of growth: Upright.
Vigor: Fast.
Productivity: Good.
Botanical characteristics of plant structures: Short, petiole, shiny cuticle.
Fertility: Commercial fertilization.
Plant shoots: Many.

Propagation

Type: By division.
Time to produce a rooted young plant, spring: 16-20 weeks.
Root description: Medium in thickness.

Plant

Growth habit: Upright.
Plant shape: Plants are full.
Height (from soil level to top of leaf plane): Approximately 30-40 cm to top of highest leaf.
Plant diameter or spread: Approximately 15 cm.
Growth rate: Rapid.

Stem description:
*Length.*—Approximately 3 inches.
*Diameter.*—Approximately 1.5 mm.
*Texture.*—Smooth.
*Branching.*—Multi.
*Colors, mature.*—Moderate to light yellow 150D.

Age of plant described: Approximately 6 months.

Foliage

Leaves:
*Arrangement.*—Simple.
*Average length.*—About 35 cm.
*Average width.*—About 15 cm.
*Shape of blade.*—Ovate.
*Apex.*—Acuminate, pointy.
*Base.*—Attenuate.
*Margin.*—Entire.
*Texture of top and bottom surface.*—Smooth.
*Color.*—Mature leaves, upper surface: Variegation, areas of 150A moderate yellow green, areas of 150D moderate to light yellow, areas of N144C olive green and 143B moderate green.
*Venation.*—Pinnately net veined.

Petiole:
*Average petiole sheath length.*—3-6 inches.
*Diameter.*—Approximately 1.5 mm.
*Strength.*—Moderate.
*Texture.*—Smooth.
*Petiole color designation.*—143B moderate green.

Flower

Blooming not observed to date on the new cultivar.

Other Characteristics

Seed production: No seed production to date has been observed.

Temperature tolerance: Low temperature tolerance to at least 50 degrees Fahrenheit, high temperatures to at most 95 degrees Fahrenheit.

Other distinctive characteristics: Overall commercially interesting appearance. 'Lucia' has variegation that includes 150A moderate yellow green, areas of 150D moderate to light yellow, areas of N144C olive green and 143B moderate green.

What is claimed is:

1. A new and distinct cultivar of *Spathiphyllum wallisii* plant named 'Lucia' as illustrated and described.

* * * * *